United States Patent
Kim et al.

(10) Patent No.: US 10,639,296 B2
(45) Date of Patent: May 5, 2020

(54) METHODS TO MITIGATE INJURY FROM RADIATION EXPOSURE

(71) Applicant: Henry Ford Health System, Detroit, MI (US)

(72) Inventors: Jae Ho Kim, West Bloomfield, MI (US); Stephen L. Brown, LaSalle (CA); Andrew Kolozsvary, Macomb, MI (US)

(73) Assignee: Henry Ford Health System, Detroit, MI (US)

(*) Notice: Subject to any disclaimer, the term of this patent is extended or adjusted under 35 U.S.C. 154(b) by 11 days.

(21) Appl. No.: 15/850,829

(22) Filed: Dec. 21, 2017

(65) Prior Publication Data

US 2018/0193307 A1 Jul. 12, 2018

Related U.S. Application Data

(63) Continuation of application No. 15/186,884, filed on Jun. 20, 2016, now abandoned, which is a continuation of application No. 13/504,585, filed as application No. PCT/US2010/054476 on Oct. 28, 2010, now abandoned.

(60) Provisional application No. 61/255,619, filed on Oct. 28, 2009.

(51) Int. Cl.
| | | |
|---|---|---|
| A61K 31/395 | (2006.01) |
| A61K 38/19 | (2006.01) |
| A61K 38/10 | (2006.01) |
| A61K 31/506 | (2006.01) |
| A61K 31/4709 | (2006.01) |
| A61P 39/00 | (2006.01) |
| A61K 31/4402 | (2006.01) |
| A61K 38/12 | (2006.01) |
| A61K 39/00 | (2006.01) |

(52) U.S. Cl.
CPC ........ *A61K 31/395* (2013.01); *A61K 31/4402* (2013.01); *A61K 31/4709* (2013.01); *A61K 31/506* (2013.01); *A61K 38/10* (2013.01); *A61K 38/12* (2013.01); *A61K 38/193* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 5,609,846 | A | 3/1997 | Goldenberg |
| 6,538,030 | B2 | 3/2003 | Chung et al. |
| 6,809,118 | B2 | 10/2004 | Chung |
| 7,435,718 | B2 | 10/2008 | Tudan et al. |
| 2002/0165123 | A1 | 11/2002 | Tudan et al. |
| 2003/0148940 | A1 | 8/2003 | Tudan et al. |
| 2004/0018968 | A1 | 1/2004 | Sgouros et al. |
| 2005/0272644 | A1 | 12/2005 | Chung |
| 2006/0223180 | A1 | 10/2006 | Bridger et al. |
| 2006/0275370 | A1 | 12/2006 | Chung et al. |
| 2009/0192082 | A1 | 7/2009 | Tudan et al. |
| 2010/0055077 | A1 | 3/2010 | Shakhov et al. |

FOREIGN PATENT DOCUMENTS

WO 20030012771 A2 2/2003

OTHER PUBLICATIONS

Abraham et al., "The CXCR4 antagonist 4F-benzoyl-TN14003 stimulates the recovery of the bone marrow after transplantation" Leukemia vol. 23 pp. 1378-1388 (Year: 2009).*
Burroughs, Lauri et al. Durable engraftment of AMD3100-mobilized autologous and allogeneic peripheral-blood mononuclear cells in a canine transplantation model, http://bloodjournal.hematologylibrary.org/, Prepublished online Aug. 16, 2005.
Zong Zhao-Wen et al: II "Recruitment of transplanted dermal multipotent stem cells to sites of injury in rats with combined radiation and wound injury by interaction" Radiation Research. vol. 170. No. 4. Oct. 2008 pp. 444-450.
Broxmeyer HE et al, "Rapid Mobilization of Murine and Human Hematopoietic Stem and Progenitor Cells With AMD3100. ACXCR4 Antagonist", The Journal of Experimental Medicine. Rockefeller University Press. US. vol. 201. No. 8. Apr. 18, 2005 (Apr. 18, 2005). pp. 1307-1318.
Bertho J Metal: "Comparison of autologous cell therapy and granulocyte-colony stimulating factor (G-CSF) injection vs. G-CSF injection alone for the treatment of acute radiation syndrome in a non-human primate model" International Journal of Radiation: Oncology Biology Physics, Pergamon Press, USA, vol. 63, No. 3, Nov. 1, 2005, pp. 911-920.
Wagemaker, Gerard et al.; "The Efficacy of Recombinant Thrombopoietin in Murine and Nonhuman Primate Models for Radiation-Induced Myelosuppression and Stem Cell Transplantation"; University, Institute of Hematology, The Netherlands; Thrombopoietin: From Molecule to Medicine Stem Cells 1998, (Supplement 12); pp. 127-141.

* cited by examiner

*Primary Examiner* — Eric Olson

(74) *Attorney, Agent, or Firm* — Sherill Law Offices, PLLC

(57) ABSTRACT

Mitigating radiation induced injury to a mammal that has been exposed to radiation by administering a pharmaceutically effective amount of a composition comprising at least one CXCR4 antagonist to the mammal.

9 Claims, 4 Drawing Sheets

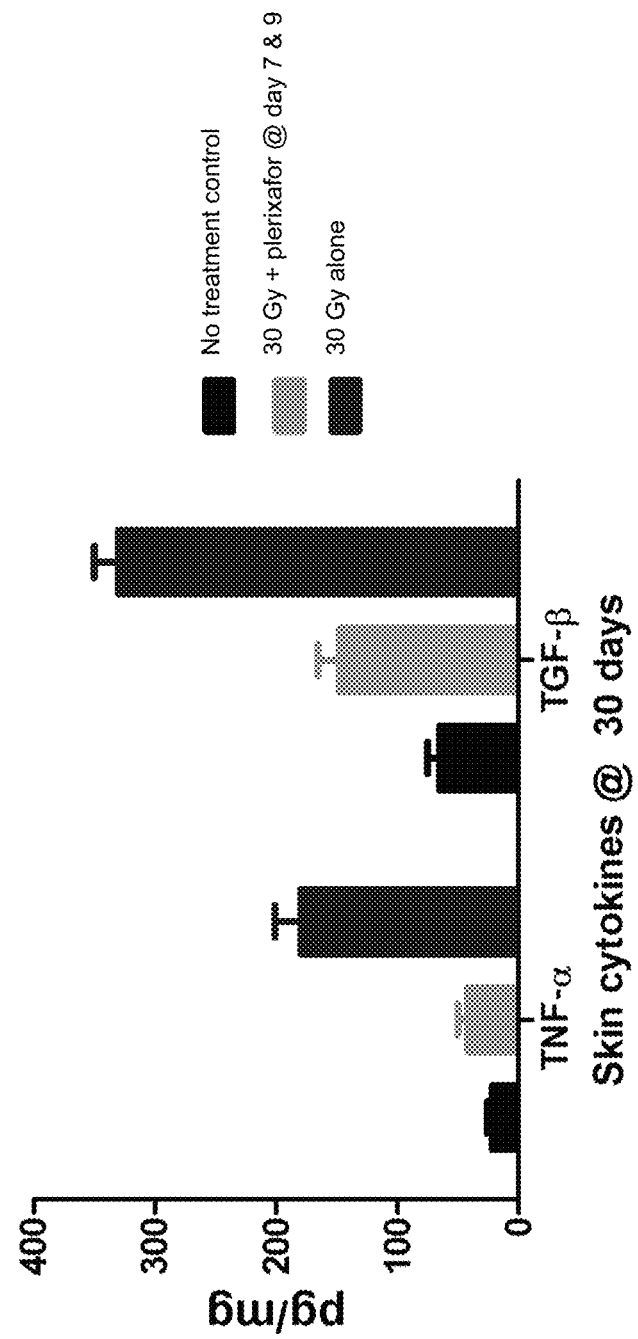

METHODS TO MITIGATE INJURY FROM RADIATION EXPOSURE

BACKGROUND

Following a (terrorist, accident, or during radiation therapy for cancer) radiation exposure either to the whole body or localized to a region of the body, tissue/organ injury results in part because of a loss of stem cells.

Peripheral blood stem cell mobilization, which has become extremely important as a source of hematopoietic stem cells for bone marrow transplantation over the last 15 years, is generally performed using the cytokine drug, G-CSF, but is ineffective in around 15 to 20% of patients. Other agents have been used to mobilize and enhance G-CSF-induced mobilization. The stem cell factor was investigated, but was withdrawn from clinical development due to its toxicity.

There is a need to develop pharmacologic agents that can reduce late tissue injury including skin in the time after a radiation exposure.

SUMMARY OF THE INVENTION

Without limiting the invention to only those embodiments expressly disclosed herein and without disclaiming any embodiments, some embodiments comprise methods to mitigate injury from radiation exposure, including without limitation, in humans.

We have demonstrated that CXCR4 antagonist mitigates injury to skin and perhaps other tissue/organs after radiation exposure.

BRIEF DESCRIPTION OF THE DRAWINGS

FIG. 3 is a graphical representation of test results from Example 4.

DETAILED DESCRIPTION OF THE INVENTION INCLUDING A BEST MODE

Figure 1:
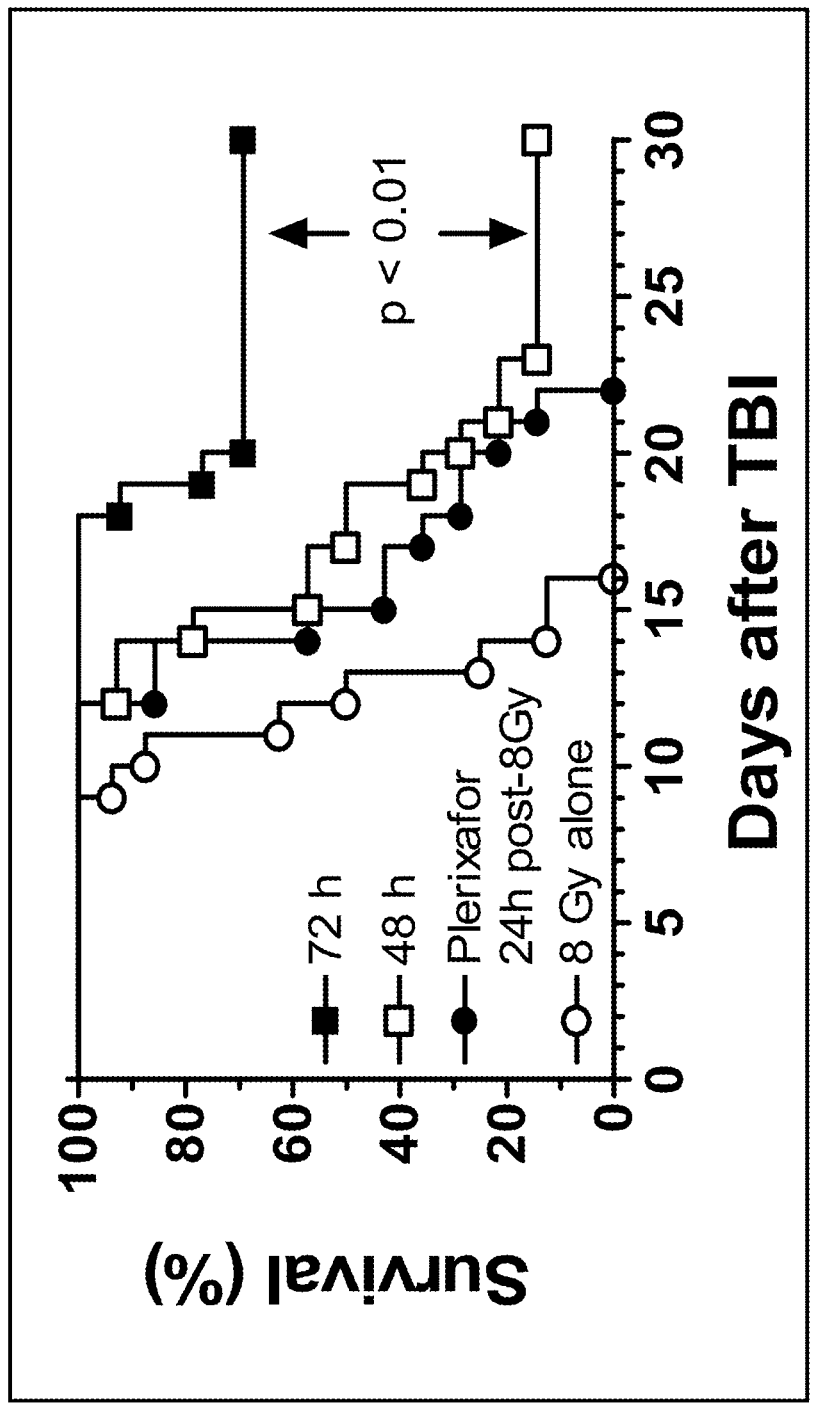
FIG. 1 is a graphical representation of test results from Example 2.

We have discovered unexpectedly that in some embodiments, without limitation, CXCR4 antagonist mitigated radiation injury of mice following irradiation. Of note, the antagonist was given starting one week after the radiation exposure. This effect may result from mobilization of stem cells, thus mitigating organ/tissue injury following radiation exposure.

To our knowledge, no other mitigator of radiation injury has been shown to be effective when started after the radiation exposure particularly when started one week after.

Among CXCR4 antagonists, AMD-3100, developed for use in the treatment of HIV, mobilizes stem cells from bone marrow niches. It has been established in the scientific literature that AMD-3100 mitigates lethality after total body irradiation in dogs. We hypothesized and experimentally verified that AMD-3100 mitigates radiation injury following localized skin irradiation, and it may mitigate radiation injury to other organs using this or a similar approach.

Use of AMD-3100 to mitigate the bone marrow syndrome after total body irradiation (TBI) is very limited. Other workers have shown that both autologous and allogeneic AMD-3100 mobilized peripheral blood mononuclear cells led to prompt and durable engraftment in dogs after lethal dose of TBI. Pharmacokinetic experiments demonstrated a rapid peak and subsequent clearance of the drug within 24 h of injection. Median days to neutrophil and platelet recoveries were 9 and 25 days, respectively. AMD-3100 administration to dogs was well tolerated without noticeable adverse effects.

AMD-3100 is a bicyclam derivative, initially developed for potential use in the treatment of HIV for its role in the blocking CXCR4, a chemokine receptor which acts as a co-receptor for certain strains of HIV. However, the CXCR4 alpha-chemokine receptor and its ligand SDF-1 are also important in hematopoietic stem cell homing to the bone marrow and in hematopoietic stem cell quiescence. The compound has been found to be a strong inducer of "mobilization" of hematopoietic stem cells from the bone marrow to the bloodstream as peripheral blood stem cells in mice, dogs, and humans. Other workers have shown that AMD-3100 could mobilize hematopoietic progenitor cells from marrow to peripheral blood in healthy human volunteers. The side effects of single-dose administration AMD-3100 to normal donors were very minor. They also showed that AMD-3100 induced rapid mobilization of mouse and human hematopoietic progenitor cells (HPC) and more importantly synergistically augmented G-CSF-induced mobilization of HPCs. Further, AMD-3100 mobilized peripheral-blood mononuclear cells were successfully engrafted to produce long-term repopulating cells.

The CXCR4 antagonist is safe in humans at the dose that produces an effect.

The development of an effective mitigator of radiation tissue/organ injury following a radiation exposure, such as CXCR4 antagonist, has the potential to benefit at least three distinct groups of individuals: (1) victims in the unfortunate event of a radiological attack or nuclear disaster; (2) clean up workers following these events; and (3) patients undergoing radiation therapy. With the former there is the additional requirement that the mitigator has its effect when administered after the radiation exposure since there may be a lack of prior knowledge of a radiological incident. In particular, use of stem cell mobilizers according to some embodiments in cancer patients undergoing radiation therapy may be substantial since the compound could potentially be administered after the tumor has been effectively treated. There are about half a million cancer patients that receive radiation therapy annually; a significant fraction of these patients receive a substantial radiation dose to normal skin tissue. There may be tens of thousands of individuals that would benefit from the effects of stem cell mobilizers to reduce the late effects of radiation on normal tissues such as skin tissue.

EXAMPLES

The following examples of some embodiments of the invention are provided without limiting the invention to only those embodiments described herein and without disclaiming any embodiments.

We have demonstrated that radiation injury can be reduced significantly by Mozobil, also known as plerixafor or AMD-3100, a CXCR4 antagonist, when the drug was applied days or even one week after the radiation exposure.

Example 1

We exposed mice to radiation, total body dose of 8 Gy at a rate of approximately 1 Gy per minute. Subsequently, days later, we administered Mozobil [I.P.] at 5 mg/kg dose as a single injection. We monitored the test mice for lethality. We found survival was significantly enhanced with Mozobil.

Example 2A

CXCR4 Antagonist Reduces Lethality Following Radiation Exposure

The CXCR4 antagonist plerixafor, given after total body irradiation (TBI) to C57BL/6 mice provides significant mitigation from TBI-induced lethality. FIG. 1 illustrates the significant enhancement in survival to an otherwise lethal radiation exposure when plerixafor was administered 3 days after the radiation.

Referring to FIG. 1, mitigation of radiation lethality by plerixafor, 5 mg/kg, I.P. increased with the duration of time delay between radiation exposure and drug administration. Survival at 30 days increased from 0% to 14% to 69% when plerixafor was administered 24 h, 48 h, and 72 h after radiation exposure, respectively. Median survival was significantly improved from 18 to beyond 30 days, when the time between radiation and drug increased from 48 to 72 h ($p<0.01$, Log rank).

We note that the enhanced survival after radiation of animals given plerixafor was consistent with the observation that mice exposed to a sublethal dose, 6.5 Gy TBI for C57BL/6 mice, had improved bone marrow cell survival 12 days after the radiation exposure. The number of endogenous spleen colonies was increased from a mean of 10±3 in C57BL/6 mice receiving a sublethal radiation dose of 6.5 Gy TBI (n=8) to a mean of 47±9 in mice given plerixafor (n=8), 5 mg/kg, 72 h after the radiation.

Example 2B

CXCR4 Antagonist Reduces Lethality Following Radiation Exposure

The survival results were confirmed in a different animal strain. Median survival of Balb/c mice improved from 13 days for mice receiving 7 Gy radiation alone to 18 days for mice receiving plerixafor, 5 mg/kg, i.p., 24 hours after 7 Gy ($p<0.01$, Log rank).

Examples 3A-3B

We exposed the legs of mice to 25 or 30 Gy radiation at a dose rate of approximately 5 Gy per minute. Subsequently, one week later, we administered Mozobil [I.P.] at 5 mg/kg dose followed by another Mozobil administration [5 mg/kg, I.P.] 48 hours later. We monitored the test mice for lesions relating to skin damage. We found skin damage was significantly reduced in mice receiving Mozobil.

Skin damage to the hind leg of C57BL/6 mice was measured using a semi-quantitative scale (TABLE ONE).

TABLE ONE

| SCORE | SKIN DAMAGE DESCRIPTION |
|---|---|
| \multicolumn{2}{c}{Semi Quantitative Scale For Evaluation Of The Lower Extremity Skin Reaction} | |
| 1.0 | No Effect. |
| 1.5 | Minimal erythema, mild dry skin. |
| 2.0 | Moderate Erythema, dry skin. |
| 2.5 | Marked erythema, start of dry desquamation. |
| 3.0 | Dry desquamation, start of skin breakdown, minimal dry crusting. |
| 3.5 | Dry desquamation, with dry crusting and superficial, minimal scabbing. |
| 4.0 | Patchy moist desquamation, moderate scabbing. |
| 4.5 | Confluent moist desquamation, ulcers, large deep scabs. |
| 5.0 | Open wound, draining, full thickness skin loss, necrosis. |

Example 3A

CXCR4 Antagonist Mitigates Radiation-Induced Skin Injury

Figure 2A:
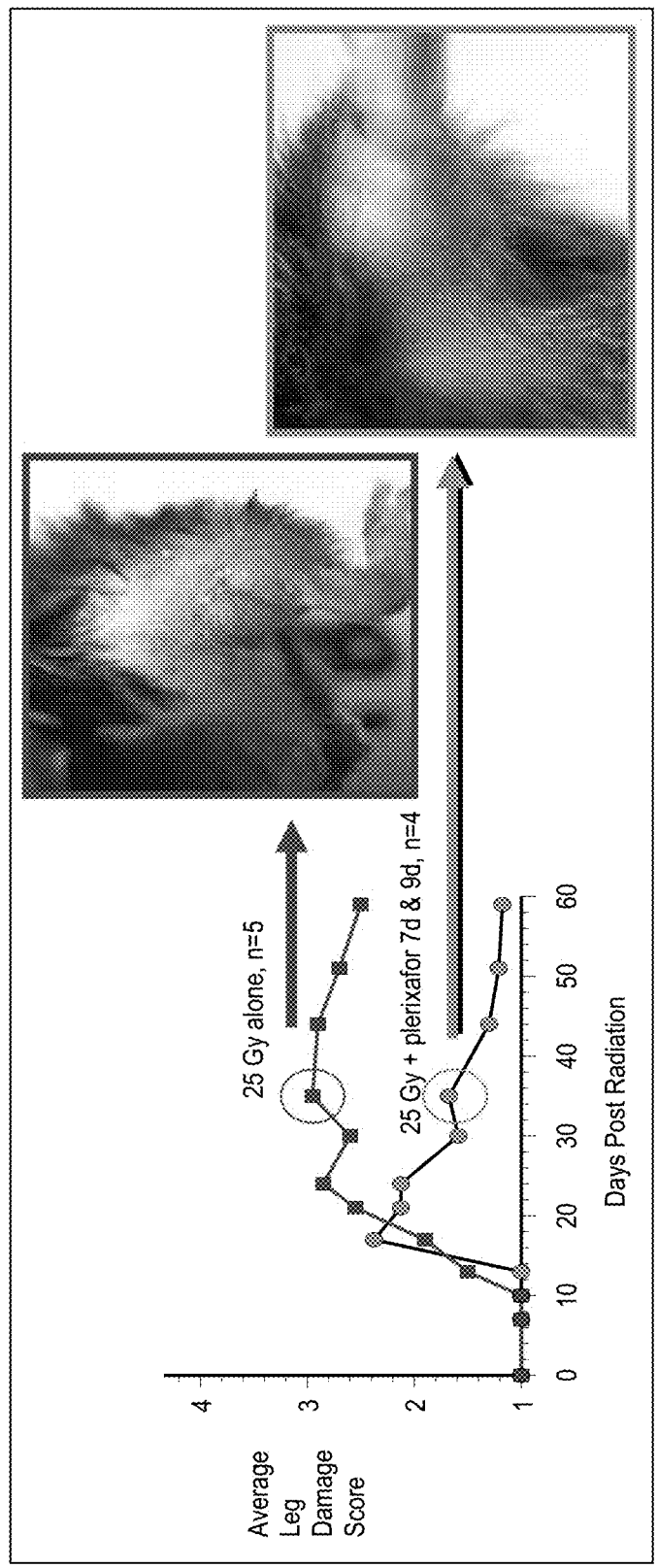
FIG. 2A is a graphical representation and photographic depiction of test results from Example 3A.

Plerixafor given 7 days after the radiation exposure was highly effective at mitigating radiation cutaneous injury. A radiation exposure of 25 Gy caused chronic cutaneous injury characterized by dry desquamation and minimal scabbing that started at about 3 weeks and persisted to 60 days. When 25 Gy radiation exposure was followed by plerixafor (5 mg/kg, I.P.) given twice starting one week after the radiation exposure followed by another dose 48 hours later, eighteen days after radiation the reaction was initially similar to radiation alone and soon resolved completely such that the legs were normal except for some hair thinning at day 60. FIG. 2A illustrates the effect at one month after 25 Gy exposure with and without plerixafor.

Example 3B

CXCR4 Antagonist Mitigates Radiation-Induced Skin Injury

Figure 2B:
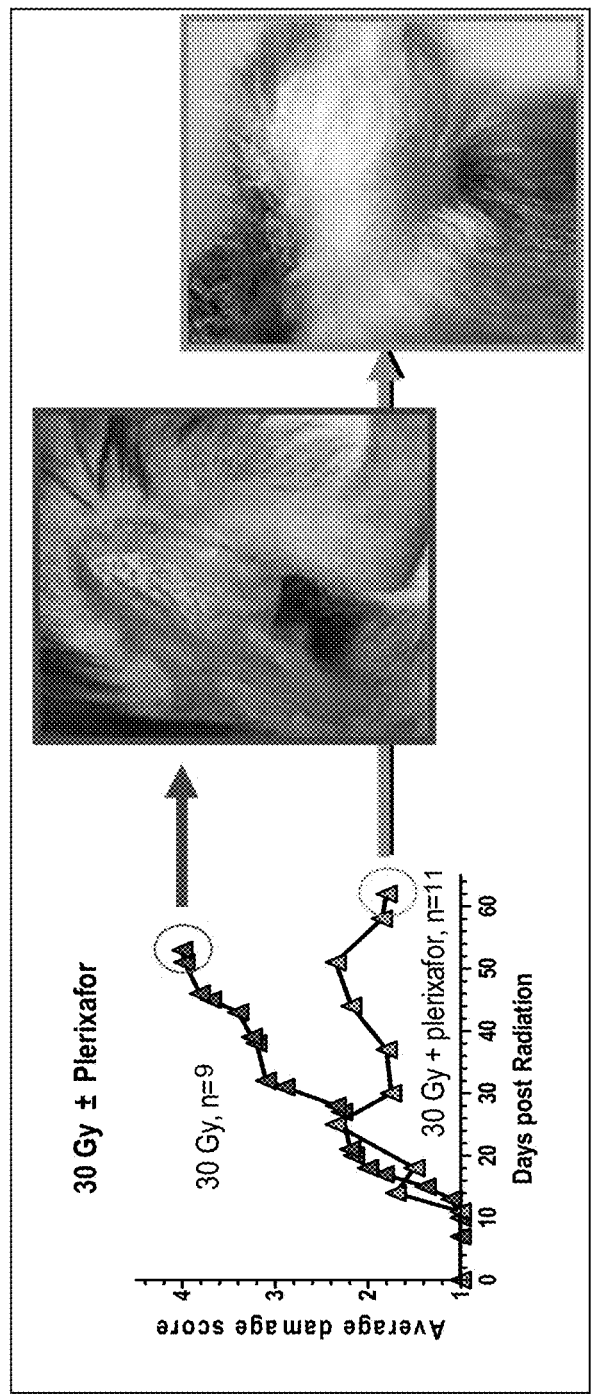
FIG. 2B is a graphical representation and photographic depiction of test results from Example 3B.

The response of mouse skin following 30 Gy plus plerixafor was even more dramatic (FIG. 2B). A radiation exposure of 30 Gy caused irreversible chronic cutaneous injury characterized by moist desquamation that started at about 3 weeks and persisted to 60 days. In contrast, mice receiving 30 Gy plus plerixafor (5 mg/kg, I.P.) given twice starting one week after the radiation exposure followed by another dose 48 hours later had some hair loss but were otherwise normal at approximately day 60.

Examples 3A and 3B (FIGS. 2A and B) illustrate the mitigating effect of plerixafor as a function of time using the semi-quantitative scale of skin reaction described in Table 1. This data was used to approximate the radiation "protection" factor, RPF, defined as the radiation dose without mitigator necessary to obtain a biological effect divided by the radiation dose with the mitigator necessary to obtain the same biological effect. For mitigation of cutaneous injury in our model, plerixafor, appears to have a RPF of better than 1.2 since 25 Gy alone yielded a slightly worse biological response than did 30 Gy plus plerixafor. We conclude that the data is suggestive of a radiation protection factor of at least 1.2 (i.e. 30 Gy/25 Gy) when plerixafor followed radiation exposure by one week.

Leg contraction assessed by the percent leg extension relative to the unirradiated leg, another endpoint of normal tissue injury related to skin damage, was also significantly improved with the administration of plerixafor (data not shown).

Example 4

CXCR4 Antagonist Reduces TGF-Beta and TNF-Alpha in Irradiated Skin

Referring to FIG. 3, skin cytokines by ELISA showed increased levels 30 days after a 30 Gy radiation exposure. There was a significant reduction compared to 30 Gy alone when irradiated mice were administered plerixafor (5 mg/kg, I.P.) on day 7 and day 9 after 30 Gy. Cytokine concentrations were from multiple samples, n=3 or 4 from single mice: one control, one receiving radiation alone and one receiving combined drug and radiation.

Our studies to date have shown that irradiated skin exhibits a significant increase in a number of cytokines including TGF-beta and TNF-alpha, which were significantly reduced by the addition of plerixafor (5 mg/kg, I.P. on day 7 and 9 post-irradiation) (FIG. 3).

The optimal results were found when the stem cell mobilizer was given starting 1 week after the radiation exposure.

The magnitude of the effect was estimated. The dose of radiation resulting in a level of radiation skin injury in the presence of stem cell mobilizer, 30 Gy, was 1.2 times higher than the radiation dose resulting in the same effect in the absence of the stem cell mobilizer, 25 Gy, suggesting mice could tolerate 20% higher doses if administered stem cell mobilizer after the radiation exposure.

Example 5

Using an autologous spleen colony assay we observed improved bone marrow cell survival after a total body radiation exposure indicating that mobilized stem cells may have the ability to mitigate radiation injury in a variety of tissues following a radiation exposure.

Accordingly, rapidly proliferating tissue such as bone marrow, skin and gastrointestinal tract are likely to benefit. This is significant because these tissues are known to be particularly susceptible to radiation injury. Other tissues which are slowly proliferating tissues such as lung and brain in which function can be preserved by a functioning subunit may be reconstituted by mobilized stem cells may also benefit from the approach.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of embodiments of the invention as disclosed. It is intended that the method within the scope of these disclosures and their equivalents be covered thereby. This description of the invention should be understood to include all novel and non-obvious combinations of elements described herein, and claims may be presented in later applications to any novel and non-obvious combination of these elements. The foregoing embodiments are illustrative, and no single feature or element is essential to all possible combinations that may be claimed in this or a later application.

Where the disclosure recites "a" or "a first" element or the equivalent thereof, such disclosure should be understood to include incorporation of one or more such elements, neither requiring nor excluding two or more such elements.

We claim:

1. A method of mitigating radiation induced injury to a mammal that has been exposed to an external source of radiation, comprising the steps of: (a) identifying a mammal that has been exposed to an external source of radiation, (b) ascertaining a time of exposure to the external source of radiation, (c) calculating a scheduled administration time by adding a delay period of at least 48 hours to the ascertained time of exposure, and (d) commencing administering a pharmaceutically effective amount of a composition comprising at least one CXCR4 antagonist to the mammal at or after the scheduled administration time, wherein the mammal is not subject to bone marrow transplantation.

2. The method of claim 1 wherein the delay period is at least 72 hours.

3. The method of claim 1 wherein the delay period is at least one week.

4. The method of claim 1 wherein the delay period is between 48 hours and one week.

5. The method of claim 1 wherein the mammal is a human.

6. The method of claim 1 wherein the CXCR4 antagonist is coadministered with a granulocyte colony-stimulating factor.

7. The method of claim 1 wherein the method mitigates radiation induced injury to tissue.

8. The method of claim 1 wherein the method mitigates radiation induced injury to organ tissue.

9. The method of claim 1 wherein the method mitigates radiation induced injury to skin.

* * * * *